(12) United States Patent
Schiffrin et al.

(10) Patent No.: US 7,217,414 B2
(45) Date of Patent: May 15, 2007

(54) METHODS OF PREVENTING PERITONITIS BY ADMINISTERING LACTIC ACID BACTERIUM

(75) Inventors: Eduardo Schiffrin, Crisser (CH); Carlos Guarner, Barcelona (ES); German Soriano, Barcelona (ES)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 10/247,841

(22) Filed: Sep. 20, 2002

(65) Prior Publication Data
US 2003/0044397 A1 Mar. 6, 2003

Related U.S. Application Data

(63) Continuation of application No. PCT/EP01/03271, filed on Mar. 22, 2001.

(30) Foreign Application Priority Data
Mar. 24, 2000 (EP) ................... 00106441

(51) Int. Cl.
*A01N 63/00* (2006.01)
*C12N 1/20* (2006.01)

(52) U.S. Cl. ................. 424/93.45; 424/9.1; 435/252.5; 435/853

(58) Field of Classification Search ............ 424/93.45, 424/9.1; 435/853, 252.9, 93.45
See application file for complete search history.

(56) References Cited

U.S. PATENT DOCUMENTS

| 5,494,664 | A | 2/1996 | Brassart et al. ............ 424/93.4 |
| 5,603,930 | A | 2/1997 | Brassart et al. ........... 424/93.45 |
| 5,716,615 | A | 2/1998 | Cavaliere Vesely et al. ...... 424/93.4 |
| 6,368,591 | B1 * | 4/2002 | Chen et al. ............... 424/93.45 |
| 6,399,124 | B1 * | 6/2002 | Lesens et al. .................. 426/61 |

FOREIGN PATENT DOCUMENTS

| EP | 0363491 A | 4/1990 |
| EP | 0577904 A | 1/1994 |
| EP | 861905 A | 10/1998 |
| JP | 04264034 | 11/1993 |
| JP | 08176000 | 9/1996 |
| JP | 09301877 | 2/1998 |
| WO | WO 96/35440 | 11/1996 |
| WO | WO 99/07393 | 2/1999 |

OTHER PUBLICATIONS

Garcia-Lafuente et al. Antiinflammatory effect of *Lactobacillus paracasei* on bowel inflammation. Gastroenterology, (Apr. 1999), vol. 116, No. 4, part 2, pp. A882.*
Lafuente et al., XP-000961243 "Anti-inflammatory Effect Of *Lactobacillus paracasei* In A Model Of Bowel Inflammation", P. A 882 p.a.. 1999.
D. Brassart et al., XP-0009611251, "The Use Of Probiotics To Reinforce Mucosal Defence Mechanisms", Trends in Food Science & Technology, vol. 8, pp. 321-326 (1997).
Mattila Sandholm et al., XP-000971026, "Probiotics: towards demonstrating efficacy", Trends in Food Science & Technology, vol. 10, pp. 393-399 (1999).
English Abstract Article by F B Kasravi et al., The effect of pretreatment with endotoxin and *lactobacilluson* bacterial translocation in acute liver injury. Department of Surgery, Lund University, European Journal Of Surgery, vol. 162 (7), pp. 537, (1996).
English Abstract Article by T. Shiina et al., "Effects of heat treated cells of intestinal lactic acid bacteria in rats fed a deoxycholic acid diet", Institute for Intestinal and Environmental Microbiology, Jikken Dobutsu. Experimental Animals, vol. 39 (3) pp. 325-335 (1990).

* cited by examiner

*Primary Examiner*—Vera Afremova
(74) *Attorney, Agent, or Firm*—Bell Boyd & Lloyd LLP

(57) ABSTRACT

The present invention relates to the use of lactic acid bacteria capable of adhering to the mucosa of the intestine and especially colonizing it for the prevention of peritonitis. In particular, the present invention relates to the use of such lactic acid bacteria for the prevention of peritonitis caused by cirrhosis of the liver. Specifically, the present invention relates to a method for preventing peritonitis in a patient in need of such prevention. This method includes administering to the patient a lactic acid bacterium that is capable of adhering to the intestine's mucosa and essentially colonizing it for the preparation of an ingestable carrier. The invention also relates to a peritonitis preventing composition of a lactic acid bacterium that is capable of adhering to the intestine's mucosa and essentially colonizing it for the preparation of an ingestable carrier. The carrier is preferably a food or pharmaceutical composition.

12 Claims, No Drawings

METHODS OF PREVENTING PERITONITIS BY ADMINISTERING LACTIC ACID BACTERIUM

CROSS-REFERENCE TO RELATED APPLICATION

This application is a continuation of the US national phase designation of International Application PCT/EP01/03271 filed Mar. 22, 2001, the content of which is expressly incorporated herein by reference thereto.

BACKGROUND ART

The present invention pertains to the use of lactic acid bacteria capable of adhering to the intestine's mucosa and essentially colonizing it for the prevention of peritonitis. In particular, the present invention relates to the use of such lactic acid bacteria for the prevention of peritonitis associated with liver cirrhosis.

Peritonitis is an inflammation of the peritoneum, attributable to a severe local infection regularly resulting from gastrointestinal inflammation and infection, gastrointestinal perforation and trauma, including surgery or peritoneal dialysis. To this end, pathogenic and potentially pathogenic microorganisms and occasionally cellular debris enter the peritoneum and elicit an immune response by the host, which may often not cope with the challenge of the pathogenic invasion.

This hold true in particular for patients suffering from liver cirrhosis. Cirrhotic patients commonly have intestinal bacterial overgrowth and a decreased immune response, which seems to be at least in part due to an inferior opsonic activity in the ascitic fluid. Advanced cirrhosis is therefore quite often accompanied by a spontaneous bacterial peritonitis (SBP) usually involving gram-negative, enteric pathogens that are normally found in the intestine. Developing SBP in the ascitic fluid is therefore deemed to be caused by bacterial translocation of intestinal bacteria into the peritoneum.

A major jeopardy of peritonitis is bacterial dissemination, i.e., the spread of the pathogens via the blood and lymph systems, resulting in the infection of diverse tissues and leading to a life-threatening situation for the affected individual. Once bacteria have entered the peritoneal cavity, dissemination is quite rapid. Within 6 minutes of intraperitonal inoculation of bacteria in dogs, thoracic lymph has been found culture-positive, while within 12 minutes elevated bacterial levels in the bloodstream may be found.

Although several advances in diagnosis and treatment of peritonitis were made still about one third of hospitalized patients with this infection eventually die from gastrointestinal bleeding, liver failure or the hepatorenal syndrome.

At present the typical medical treatment for the prevention and/or treatment of peritonitis includes antibiotic therapy, especially prior to surgical procedures. This approach suffers, however, from the drawback of developing drug resistant bacteria known to cause peritonitis. Moreover, since both gram-positive and gram-negative microorganisms may cause peritonitis, the use of an antibiotic may not be sufficient in all cases.

In addition, antibiotic treatment is non-specific, also exterminating many non-pathogenic microorganisms that commonly prevent bacterial diseases through bacterial antagonism, in particular in the gastrointestinal tract. Therefore, in applying broad spectrum antibiotics for prolonged periods the growth of most of the bacteria thriving in the intestinal tract is suppressed with the result of antibiotic resistant strains of pathogenic micro-organisms freely propagating. As a consequence, antibiotics may occasionally foster peritonitis, rather than prevent it.

Another approach for the treatment of peritonitis is disclosed in International application WO 97/00081. This document suggests the use of antagonists to CD14, a surface antigen known to interact with lipopolysaccharides of bacterial origin. Bacterially derived lipopolysaccharides are known to be capable to stimulate the immune system by binding to cell surface receptors of cells of the immune system which in turn start to produce and secrete cytokines and other mediators, that stimulate the immune system. However, these cytokines or mediators, respectively, have also been found to be able to support bacterial growth and invasiveness. The gist of the treatment proposed therefore lies in an interruption of the early immune response during which the cytokines/mediators are produced. It is thought that in essentially preventing the production of the cytokines by blocking activation via CD14 the growth of the bacteria is not promoted as well. Yet this method suffers from the drawback that the immune response is essentially impeded as well, so that the host's own defense mechanism is deteriorated.

Consequently, there is a need for an effective method for the prevention and/or treatment of local infections, such as those associated with peritonitis, and this need is satisfied by the present invention.

SUMMARY OF THE INVENTION

During the extensive experimentation leading to the present invention, the inventors have investigated the theory whether lactic acid bacteria in the gut of an individual may have a positive influence on the cells of the immune system in the peritoneum, especially on the cells of the immune system adjacent to the intestine. It has been found that the administration of particular lactic acid bacteria obviously reduce the number of bacterial counts in the ascites and the peritoneum, respectively, of animals suffering from peritonitis, showing that lactic acid bacteria, in particular probiotic lactic acid bacteria are able to efficiently decrease intestinal bacterial overgrowth and translocation of pathogens.

The above problem has therefore been solved by providing the use of lactic acid bacteria that are capable of adhering to the intestine's mucosa and essentially colonizing it for the preparation of an carrier for preventing peritonitis. Accordingly, the present invention relates to a method for preventing peritonitis in a patient in need of such prevention. This method comprises administering to the patient a lactic acid bacterium that is capable of adhering to the intestine's mucosa and essentially colonizing it for the preparation of an ingestible carrier. The invention also relates to a peritonitis preventing composition comprising a lactic acid bacterium that is capable of adhering to the intestine's mucosa and essentially colonizing it for the preparation of an ingestible carrier. In this method and composition, the carrier is a food or pharmaceutical composition.

DETAILED DESCRIPTION OF THE PREFERRED EMBODIMENTS

The peritonitis may be a spontaneous bacterial peritonitis (SBP) such as is caused by the sudden appearance of potential pathogens in the peritoneum. This often concurs with a deficiency of liver function, such as during a cirrhotic state thereof. Moreover the peritonitis may well be virally induced or a peritonitis following dialysis or surgery.

According to a preferred embodiment of the invention, the lactic acid bacterium is a probiotic lactic acid bacterium, preferably one selected from the genus *Lactobacillus* or *Bifidobacterium*, and is more preferably *Lactobacillus johnsonii* CNCM I-1225, *Lactobacillus paracasei* CNCM I-2116 or *Bifidobacterium* CNCM I-2168.

The *Lactobacillus johnsonii* (La1), *Lactobacillus paracasei* (NCC 2461), and *Bifidobacterium* (NCC 251) strains were deposited by way of example under the Budapest Treaty at the Collection Nationale de Cultures de Microorganismes (CNCM), Institut Pasteur, 28 rue du Docteur Roux, 75724 Paris Cédex 15, France. These strains were deposited on Jun. 30, 1992 (La1), Jan. 12, 1999 (NCC 2461), and Mar. 15, 1999 (NCC 251), under the references CNCM I-1225, CNCM I-2116, and CNCM I-2168, respectively.

According to the present invention, the lactic acid bacterium to be used is incorporated in a carrier which may be a food or a pharmaceutical product, such as e.g. milk, yoghurt, curd, cheese, fermented milks, milk based fermented products, ice-creams, fermented cereal based products, milk based powders, or infant formulae. The carrier may be in the form of tablets, liquid bacterial suspensions, dried oral supplements, wet oral supplement, dry tube feeding or wet tube feeding etc.

The carrier may well include other compounds known to be beneficial to an impaired situation of the gut, e.g., antioxidants, such as Vitamin C, Vitamin E, Selenium or Zinc. Depending on the respective preventive therapy the person skilled in the art will choose the appropriate galenic form and/or supplements, thus assisting in improving the individual's health.

Without being bound to any theory, the activity of the microorganism is believed to be mainly due to two factors:

Probiotics are known to have a beneficial effect on the host's immune system. In the present case it seems as if the lactic acid bacteria are capable to stimulate the immune system in the peritoneum and in particular the non-specific immune defense, located around the individual's gut to combat microorganisms invading the peritoneum through the intestine's walls. This immune barrier is normally weakened in patients suffering from liver cirrhosis.

On the other hand, it is thought that the lactic acid bacteria colonizing the intestine's wall will physically prevent or at least reduce the number of potential pathogens invading the peritoneum via the gut. Through adhesion to the intestine the bacteria obviously establish a close contact with the intestinal mucosa masking receptors of the intestine's surface for pathogens.

As will be appreciated, the activity of the microorganisms is dose dependent with the effect that the more microorganisms are incorporated by means of ingesting the food or pharmaceutical composition, respectively, the higher the protective and/or curing activity. Thus, the food or pharmaceutical composition to be used according to the present invention may contain the lactic acid bacterium in an amount from about $10^5$ cfu/g to about $10^{12}$ cfu/g carrier. For the purpose of the present invention, the abbreviation "cfu" shall designate a "colony forming unit" that is defined as the number of bacterial cells as revealed by microbiological counts on agar plates.

Since the micro-organisms used are not obnoxious to mankind and animals and have eventually been isolated from a natural surrounding, namely baby feces, a high amount thereof may be incorporated so that essentially a high proportion of the individual's intestines may be colonized by the micro-organisms.

EXAMPLES

The invention will now be described by means of examples that are not construed to limit it to the embodiments.

Example 1

Treatment of Animals

A total of 31 male Sprague-Dawley rats were included in the study with 19 thereof being made cirrhotic by weekly intragastric administration by gavage of carbon tetrachloride and water with phenobarbital (1.5 mmol/l) ad libitum. The diet has been standard B&K (Barcelona, Spain) and was available for the rats ad libitum. The 12 rats from control group received standard diet (supra) and water with phenobarbital during all the study, while the other rats (19) of the test group received the standard diet inclusive the lactic acid bacterium CNCM I-1225 (*Lactobacillus johnsonii*, La1) in an amount of about $10^{10}$ cfu/day or water.

All control rats were killed 18 weeks after they began to drink water with phenobarbital. From 12 control rats, 6 received treatment A (water) and 6 treatment B (water plus *lactobacillus*). The treatment was administered by gavage. Laparotomy was performed under anesthesia after 10 days of respective treatment or no treatment and samples of cecal feces, ileal feces, ileum wall, mesenteric lymph nodes and ascitic and pleural fluid were collected for the microbiological study. Blood was collected from cava vein to determine endotoxemia. In addition, samples of ileal wall, cecal wall, spleen and liver were collected for histological study, and portal pressure was assessed both by portal vein puncture and the ratio spleen weight/rat weight.

With the test group, when rats developed ascites (approximately after 20 weeks of the beginning of the induction of cirrhosis), a paracentesis under anesthesia was performed to verify the presence of ascites, and they were distributed by randomization into two groups: one group (n=8) received treatment A (water) and another group (n=11) received treatment B (plus lactic acid bacterium). Treatment was administered by gavage. The procedures at the end of the study (after 10 days of treatment) were the same than in control rats.

A study of intestinal permeability by the determination of lactulose and mannitol in urine was performed to all the control and cirrhotic rats during the 24 hours previous to the beginning of treatment and at the end of treatment. Moreover, the study of intestinal permeability was performed to all the control and cirrhotic rats every 4 weeks through the period of induction of cirrhosis or control.

Example 2

Presence of Ascites, Bacterial Translocation and Bacterial Peritonitis

At the moment of laparotomy, 7/8 cirrhotic rats treated with water (treatment A) and 7/11 cirrhotic rats with treatment B had detectable ascitic fluid. Cultures of mesenteric lymph nodes were negative in all 22 control rats. Cultures of mesenteric lymph nodes, ascitic fluid and pleural fluid were also negative in all cirrhotic rats receiving treatment B. Considering cirrhotic rats receiving water, 5/8 rats showed bacterial translocation (positive cultures) to mesenteric lymph nodes or ascitic or pleural fluid (p<0.01 with respect to groups receiving treatment A and B): 2 to pleural fluid, 2 to mesenteric lymph nodes, and 1 to pleural and ascitic fluid and to mesenteric lymph nodes. Bacteria isolated were: 2 *Escherichia coli*, 2 *E. coli+enterococcus*, and 1 *E. coli+ streptococcus*.

The results are summarized in table I below:

TABLE I

|  | Treatment A (water) (n = 8) | Treatment B (+ Lactic acid bacterium) (n = 11) |
|---|---|---|
| Ascites | 7/8 | 7/11 |
| Mesenteric lymph nodes | 3 | 0 |
| Ascitic fluid | 2 | 0 |
| Pleural fluid | 2 | 0 |
| Total | 7/8 | 0/11 |

From these results it becomes obvious that bacterial translocation significantly decreased in cirrhotic rats receiving *L. johnsonii* CNCM 1225 as compared to cirrhotic rats receiving water.

Example 3

Microbiological Intestinal Study

In this study various microorganisms were tested for in the control and the cirrhotic rats treated as indicated in Examples 1 and 2 above. Results are shown in Table II.

TABLE II

| log10 CFU/g | CONTROL RATS TREATMENT B N = 6 | CIRRHOTIC RATS | |
|---|---|---|---|
| | | WATER n = 8 | TREATMENT B N = 11 |
| Cecal Bacteroides | 5.1 ± 0.7 | 7.9 ± 0.5 | 7.4 ± 0.4 |
| Cecal Bifidus | 3.72 ± 0.29 | nd | <3.3 |
| Cecal Lactobacillus | 7.3 ± 0.1 | nd | 8.0 ± 0.2 |
| Cecal Enterococcus | 3.8 ± 0.1 | 5.8 ± 0.2 | 4.6 ± 0.3# |
| Cecal Enterobacteri | 4.3 ± 0.2 | 5.7 ± 0.3 | 4.8 ± 0.5 |
| Ileal Bacteroides | 4.2 ± 0.6 | 5.7 ± 0.9 | 4.7 ± 0.3 |
| Ileal Bifidus | <3.3 | | <3.3 |
| Ileal Lactobacillus | 7.3 ± 0.1 | 6.4 ± 0.4 | 7.8 ± 0.3 |
| Ileal Enterococcus | 3.5 ± 0.1 | 6.1 ± 0.5 | 3.7 ± 0.2## |
| Ileal Enterobacteri | 3.4 ± 0.0 | 5.3 ± 0.6 | 3.7 ± 0.6# |
| Ileal wall Bacteroides | 3.3 ± 0.0 | 3.8 ± 0.5 | 3.8 ± 0.2 |
| Ileal wall Bifidus | <3.3 | | <3.3 |
| Ileal wall Lactobacillus | 5.6 ± 0.2 | | 6.4 ± 0.3 |
| Ileal wall Enterococcus | <3.3 | 4.4 ± 0.6 | <3.3## |
| Ileal wall Enterobacteri | 3.4 ± 0.1 | 3.5 ± 0.2 | <3.3 |

*p < 0.01, p < 0.001 and *p < 0.03 with respect to cirrhotic rats treated with water (Mann-Whitney test).
p < 0.05 and ##p < 0.01 with respect to cirrhotic rats treated with water.
nd = not determined The above data also confirm the impaired intestinal microbial balance, i.e. intestinal bacterial overgrowth of potentially pathogenic bacteria in cirrhotic rats as compared to control rats. Treatment B decreased bacterial counts of enterobacteria and *enterococcus* and increased *lactobacillus* when compared to rats treated with water. Therefore, treatment B may correct the bacterial overgrowth of potentially pathogenic bacteria in cirrhotic rats.

The invention claimed is:

1. A method for decreasing spontaneous bacterial peritonitis (SBP), virally induced peritonitis or dialysis induced peritonitis (DIP) in a patient having liver cirrhosis, the method comprising orally administering to the patient an ingestible carrier that includes a single strain of a lactic acid bacterium in a therapeutically effective amount wherein the bacterium adheres to the intestine's mucosa and colonizes it, wherein the bacterium is *Lactobacillus johnsonii* CNCM I-1225.

2. The method according to claim 1, wherein the lactic acid bacterium is a probiotic bacterium.

3. The method according to claim 1, wherein the lactic acid bacterium is associated with the carrier in an amount from about $10^5$ cfu/g to about $10^{12}$ cfu/g carrier.

4. The method according to claim 1, wherein the bacterium is present in the carrier in an amount from about $10^5$ cfu/g to about $10^{12}$ cfu/g carrier.

5. The method according to claim 3, wherein the carrier containing the lactic acid bacterium is a food or pharmaceutical composition.

6. The method according to claim 3, wherein the carrier is a food composition selected from milk, yoghurt, curd, cheese, fermented milks, milk based fermented products, ice-creams, fermented cereal based products, milk based powders, infant formulae, tablets, liquid bacterial suspensions, dried oral supplement, wet oral supplement, dry tube feeding or wet tube feeding.

7. A method for decreasing peritonitis associated with liver cirrhosis in a patient with liver cirrhosis, the method comprising orally administering to the patient an ingestible carrier that includes a single strain of a lactic acid bacterium in a therapeutically effective amount wherein the bacterium adheres to the intestine's mucosa and colonizes it, wherein the bacterium is *Lactobacillus johnsonii* CNCM I-1225.

8. The method according to claim 7, wherein the lactic acid bacterium is a probiotic bacterium.

9. The method according to claim 7, wherein the lactic acid bacterium is associated with the carrier in an amount from about $10^5$ cfu/g to about $10^{12}$ cfu/g carrier.

10. The method according to claim 7, wherein the bacterium is present in the carrier in an amount from about $10^5$ cfu/g to about $10^{12}$ cfu/g carrier.

11. The method according to claim 9, wherein the carrier containing the lactic acid bacterium is a food or pharmaceutical composition.

12. The method according to claim 9, wherein the carrier is a food composition selected from milk, yoghurt, curd, cheese, fermented milks, milk based fermented products, ice-creams, fermented cereal based products, milk based powders, infant formulae, tablets, liquid bacterial suspensions, dried oral supplement, wet oral supplement, dry tube feeding or wet tube feeding.

* * * * *